United States Patent
Prasad Rath et al.

(10) Patent No.: US 9,913,606 B2
(45) Date of Patent: Mar. 13, 2018

(54) METHOD AND SYSTEM FOR DETERMINING HEALTH CONDITION OF A SUBJECT

(71) Applicant: Wipro Limited, Bangalore (IN)

(72) Inventors: Satish Prasad Rath, Bangalore (IN); Upendra Suddamalla, Anantapur Dt. (IN)

(73) Assignee: Wipro Limited, Bangalore (IN)

( * ) Notice: Subject to any disclaimer, the term of this patent is extended or adjusted under 35 U.S.C. 154(b) by 623 days.

(21) Appl. No.: 14/575,449

(22) Filed: Dec. 18, 2014

(65) Prior Publication Data

US 2016/0081604 A1 Mar. 24, 2016

(30) Foreign Application Priority Data

Sep. 24, 2014 (IN) .......................... 4654/CHE/2014

(51) Int. Cl.
*A61B 5/1455* (2006.01)
*A61B 5/16* (2006.01)
*A61B 5/00* (2006.01)

(52) U.S. Cl.
CPC .......... *A61B 5/165* (2013.01); *A61B 5/14551* (2013.01); *A61B 5/7271* (2013.01); *A61B 5/6822* (2013.01); *A61B 5/6833* (2013.01)

(58) Field of Classification Search
CPC .............. A61B 5/1455; A61B 5/14551; A61B 5/14552; A61B 5/72; A61B 5/7271
See application file for complete search history.

(56) References Cited

U.S. PATENT DOCUMENTS

| | | | |
|---|---|---|---|
| 6,240,309 B1 * | 5/2001 | Yamashita | A61B 5/14552 600/473 |
| 8,463,348 B2 * | 6/2013 | Cheng | A61B 5/14553 600/324 |
| 9,326,712 B1 * | 5/2016 | Kiani | A61B 5/14552 |

* cited by examiner

*Primary Examiner* — Eric Winakur
(74) *Attorney, Agent, or Firm* — LeClairRyan, a Professional Corporation

(57) ABSTRACT

Embodiments of the present disclosure disclose a method and system for determining health condition of a subject. First step of the method comprises receiving, by a computing unit, a first oxygen saturation level and a second oxygen saturation level from at least two sensors placed on the subject. Second step of the method comprises determining cerebral extraction of oxygen using the first and second oxygen saturation levels. Third step of the method comprises comparing the cerebral extraction of oxygen with a threshold level. Fourth step of the method comprises identifying a mental fatigue level of the subject based on outcome of the comparison, wherein the mental fatigue level indicates the health condition of the subject.

18 Claims, 9 Drawing Sheets

METHOD AND SYSTEM FOR DETERMINING HEALTH CONDITION OF A SUBJECT

This application claims the benefit of Indian Patent Application No. 4654/CHE/2014 filed Sep. 24, 2014, which is hereby incorporated by reference in its entirety.

FIELD

The present subject matter is related in general to health monitoring and, more particularly, but not exclusively, to a method and a system for determining mental fatigue level of a subject.

BACKGROUND

Human fatigue is a temporary inability to maintain optimal cognitive performance. The onset of human fatigue during any cognitive activity is gradual, and depends upon an individual's cognitive ability, and also upon other factors, such as sleep deprivation and overall health. Human fatigue has also been shown to adversely affect physical performance.

In recent years, experts have been emphasizing importance of objective assessment of human fatigue for preventing deaths caused by accidents and overwork in the automotive and occupational fields. For an example in mining industry, the driver of a truck who is on extended work durations need to be attentive to avoid any kind of accidents during the transportation to avoid any loss of assets, life and production time. Similarly, in case of a stock trader, who is involved in trading the equity of high values very frequently needs to be attentive to take appropriate decisions quickly to reduce big losses. Detection of fatigue is critical in various other fields of work also, such as, mining aviation, etc. Upon assessing such fatigue, it is important to make the assessment in real time in practical situations, and to notify the user to pay attention to his fatigue, instead of the conventional fatigue assessments made in laboratories. However, the conventional assessments methods were not non-invasive, non-restraint, or simple, making the methods difficult to use in practical assessments.

Existing techniques usually measure some physiological parameters related to eye and/or a body part, pressure. Electro Cardiography (ECG), etc. and then try to correlate them to deduce to an overall fatigue of the person. Such measurement techniques cause much inconvenience to the person. Additionally, the existing measurements are more of assessing the physical fatigue and not for calculating the mental fatigue of the person. The physical fatigue was evaluated relatively easily in reference to some external indices such as muscular weakness, whereas mental fatigue was evaluated mostly by carrying out surveys or the like. Therefore, it has always been difficult to exclude arbitrariness from mental fatigue evaluation.

Also, the present techniques do not detect mental fatigue levels using non-invasive methods. Hence, it becomes difficult to continuously monitor a person's stress levels and ability to maintain optimal performance.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

Disclosed herein is a method for determining health condition of a subject. The method comprises receiving, by a computing unit, a first oxygen saturation level and a second oxygen saturation level from at least two sensors placed on the subject. Then, the method determines cerebral extraction of oxygen using the first and second oxygen saturation levels. Further, the method comprises comparing the cerebral extraction of oxygen with a threshold level and identifying a mental fatigue level of the subject based on outcome of the comparison. The mental fatigue level indicates the health condition of the subject.

In an aspect of the present disclosure, a system for determining health condition of a subject is disclosed. The system comprises a processor and a memory communicatively coupled to the processor. The memory stores processor-executable instructions which on execution, causes the processor to receive a first oxygen saturation level and a second oxygen saturation level from at least two sensors placed on the subject. Then, the processor determines cerebral extraction of oxygen using the first and second oxygen saturation levels. Further, the processor compares the cerebral extraction of oxygen with a threshold level and identifies a mental fatigue level of the subject based on outcome of the comparison. The mental fatigue level indicates the health condition of the subject.

In another aspect of the present disclosure, a non-transitory computer readable medium for generating interaction diagrams for a process is disclosed. The non-transitory computer readable medium includes instructions stored thereon that when processed by a processor causes a system to perform one or more acts. First act is receiving a first oxygen saturation level and a second oxygen saturation level from at least two sensors placed on the subject. Next, act is to determine cerebral extraction of oxygen using the first and second oxygen saturation levels. Next, act is to compare the cerebral extraction of oxygen with a threshold level and identify a mental fatigue level of the subject based on outcome of the comparison. The mental fatigue level indicates the health condition of the subject.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1A:
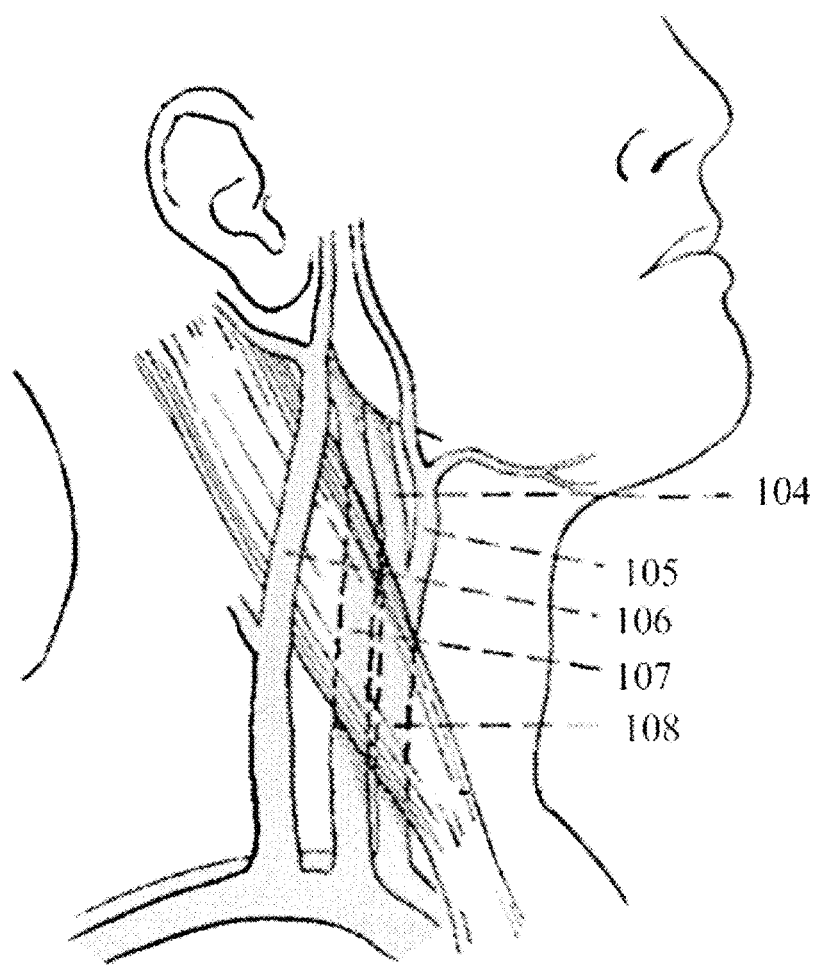
FIG. 1A is a schematic illustration of the neck region of a human body.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Embodiments of the present disclosure are related to a method and a system for determining health condition of a subject. In particular, the present disclosure relates to determining mental fatigue level of a subject. The subject may be one of human being and animal. In the present disclosure, human being has been used as an exemplary subject to explain the working of the present disclosure. Further, some of the basic vascular anatomy associated with the cardiovascular system of human being is illustrated in FIG. 1A. FIG. 1A is a schematic illustration of the neck region of a human body showing some of the major arteries and veins of the cardiovascular system. In an embodiment, common carotid arteries 108 are arteries that supply the head and neck including brain with oxygenated blood. The common carotid artery 108 divides in the neck to form the internal carotid artery 104 and external carotid artery 105. The jugular veins are veins that bring deoxygenated blood from the head back to the heart. Each side of the neck has two jugular veins, external jugular vein 106 and internal jugular vein 107. The external jugular vein 106 carries blood from the face, neck, and scalp and has two branches, posterior and anterior. The internal jugular vein 107 receives blood from the brain, the deeper tissues of the neck and the interior of the skull.

The method disclosed in the present disclosure measures the oxygen levels consumed by the brain while the subject is continuously performing the activity. Here, the activity indicates a task performed by the subject continuously which involves taking appropriate decisions, for example driving, technician in an assembly line, stock trader, etc. In an embodiment, the method comprises sensing oxygen saturation level in a noninvasive manner by using one or more sensors on the body of the subject. Then, the sensed oxygen saturation level is collected using a data aggregator. The data aggregator transmits the oxygen saturation levels to a computing unit. The computing unit computes Cerebral Extraction of Oxygen (CEO2) indicating the oxygen levels of the blood flowing through the brain. The cerebral extraction of oxygen is then compared with a threshold level to identify a mental fatigue level of the subject. In an embodiment, the threshold levels may be personalized for each subject using the historical fatigue trends. Finally, the mental fatigue level of the subject is displayed on a display unit. In an embodiment, a measurement error may be detected while determining the mental fatigue level.

The term "health condition" includes, but not limited to fatigue of the subject. The term "fatigue" in ordinary describes a very common phenomenon. For purpose of this disclosure "fatigue" comprises and may be defined as: —awareness of a decreased capacity for physical and/or mental activity due to an imbalance in the availability, utilization, and/or restoration of resources needed to perform activity—a state of weariness related to reduced motivation a transitional state between wakefulness and sleep physical state of disturbed homeostasis due to work or stress, which manifest in loss in efficiency and a general disinclination to work—a feeling of weariness and inability to mobilize energy Onset of fatigue is associated with increased anxiety, decreased short term memory, slowed reaction time, decreased work efficiency, reduced motivational drive, decreased vigilance, increased variability in work performance, increased errors and omissions which increase when time pressure, diminishing of information processing and sustained attention. The term "fatigue" used in the disclosure may be understood to comprise also any term mentioned below so for purposes of this disclosure. Following terms characterizing fatigue may be considered as synonyms. They are: exhaustion, lack of motivation, tiredness, boredom, sleepiness, feeling tired and listless, apathy, indifference, inertia, lethargy, stolidity, vacancy, drowsiness, depletion, feeling weary, feeling tired, strained or sleepy, being tired, being sleepy, being drained, being worn out, being spent, overworked. Also, fatigue can be suitably understood as opposite to following terms: vigilance, alertness, watchfulness, and wakefulness. Any of these terms as for example lack of vigilance, lack of alertness, can be also suitably treated as replacement of word fatigue in accordance with this disclosure.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1B:
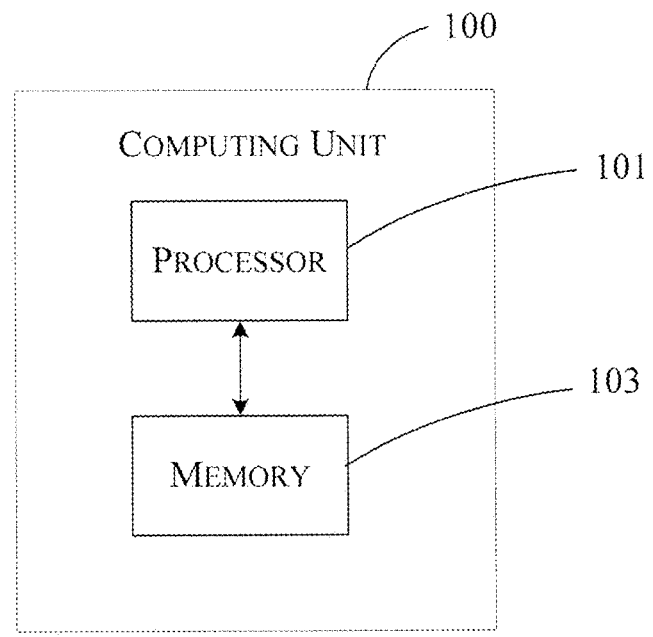
FIG. 1B illustrates a block diagram of an exemplary computing unit to monitor health condition of a subject in accordance with some embodiments of the present disclosure.

FIG. 1B illustrates an exemplary computing unit 100 or health monitoring computing device for determining health condition of a subject in accordance with some embodiments of the present disclosure. The computing unit 100 may include at least one central processing unit ("CPU" or "processor") 101 and a memory 103 storing instructions executable by the at least one processor 101. The instructions configure the processor 101 to receive oxygen saturation levels from a plurality of sensors placed on the subject. The subject may be one of human being and animal.

The processor 101 may comprise at least one data processor for executing program components for executing user- or system-generated requests. A user may include a person, a person using a device such as those included in this disclosure, or such a device itself.

The sensors measure oxygen saturation levels of the subject. In an example, the sensors are configured on a patch which is positioned on the neck of the subject. In an embodiment, a first sensor captures a first oxygen saturation level (SaO2) in the incoming blood flow to brain via carotid artery of the subject. A second sensor captures a second oxygen saturation level (SjvO2) in an outgoing blood flow from brain via jugular vein of the subject. The first and second oxygen saturation levels are measured simultaneously at a predefined interval of time to determine the oxygen levels consumed by the brain. Initially, the processor 101 determines cerebral extraction of oxygen based on the first and second oxygen saturation levels from the sensors. The cerebral extraction of oxygen is determined by calculating a difference between the first and second oxygen saturation levels as shown below.

$$CEO2_i = (((SaO_2)_i - (SjvO_2)_i)/(SaO_2)_i) * 100 \quad (1)$$

where 'i' indicate $i^{th}$ sample in the time sequence.

The trend of CEO2 indicates the oxygen consumption of brain and mental stress over a period of time.

Thereafter, the processor 101 generates a mental fatigue level by comparing the cerebral extraction of oxygen with a predefined threshold level. The mental fatigue level indicates the health condition of the subject. If the values of CEO2 are above a threshold level for a predefined interval of time, then the mental fatigue of the subject is detected.

In some embodiments of the present disclosure, the computing unit 100 may comprise an alert system (not shown) for generating an alarm. The alarm may be generated if the mental fatigue level is substantially close to or greater than the predefined threshold level.

Figure 2A:
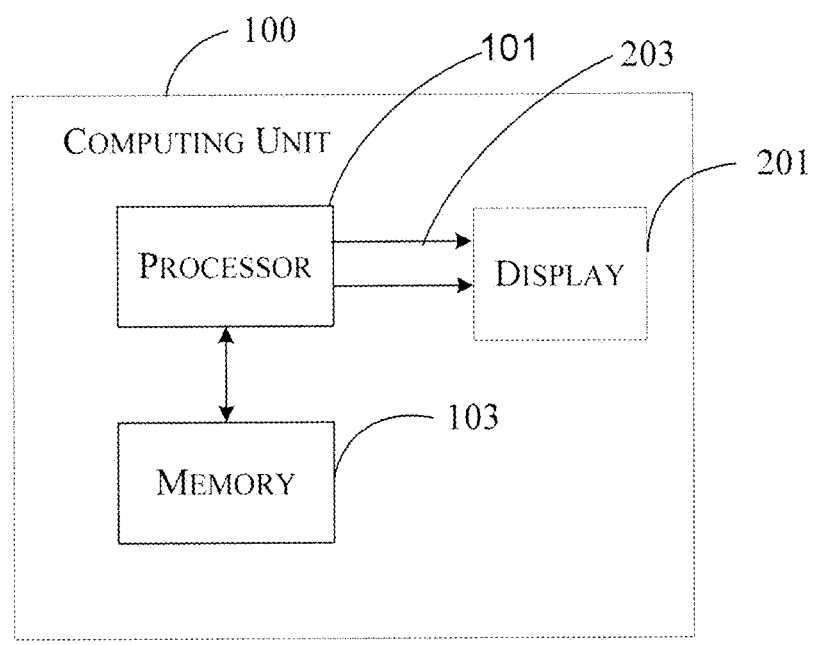
FIG. 2A illustrates a block diagram of an exemplary computing unit to monitor health condition of a subject and display the mental fatigue level on an associated display in accordance with some embodiments of the present disclosure.
Figure 2B:
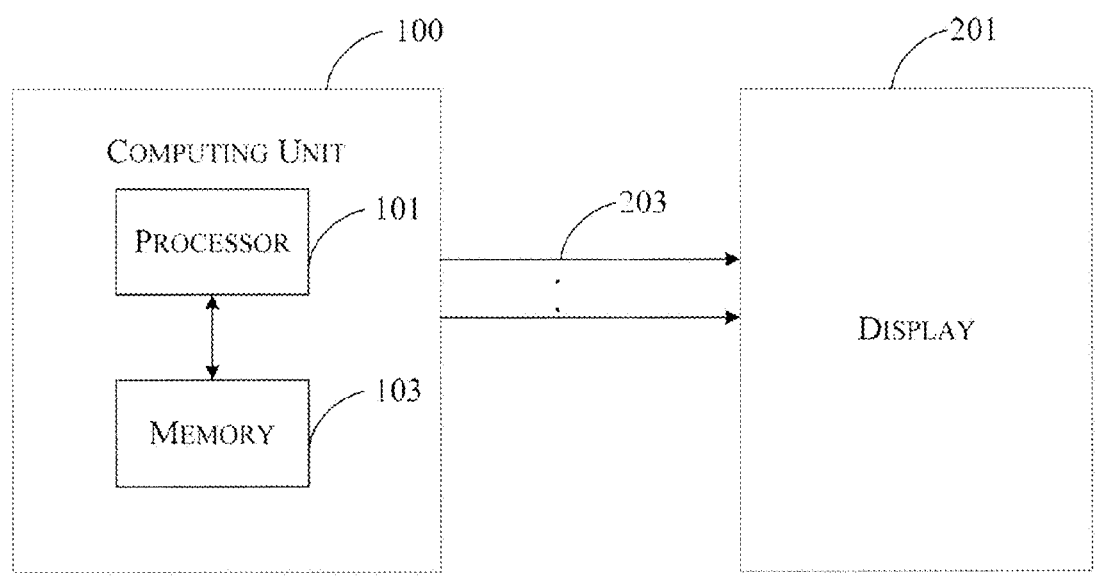
FIG. 2B illustrates a block diagram of an exemplary computing unit to monitor health condition of a subject and an associated display unit for displaying mental fatigue level in accordance with some embodiments of the present disclosure.

FIGS. 2A and 2B illustrates a computing unit 100 to monitor health condition of a subject and display the mental fatigue level on an associated display unit, in accordance with some embodiments of the present disclosure. In some embodiments, the computing unit 100 may comprise at least one processor 101, a memory 103 storing instructions executable by the at least one processor 101 and a display unit 201 for displaying mental fatigue information 203 of at least one subject, as shown in FIG. 2A. In some embodiments, the computing unit may comprise at least one processor 101, a memory 103 storing instructions executable by the at least one processor 101 and an associated external display unit 201 for displaying mental fatigue information 203 of at least one subject, as shown in FIG. 2B. The computing unit 100 transmits the mental fatigue information 203 such as, but not limited to, mental fatigue level, number of subjects for which fatigue score is generated, to the display unit 201. The display unit 201 displays the fatigue information, as received from the computing unit 100.

Figure 3A:
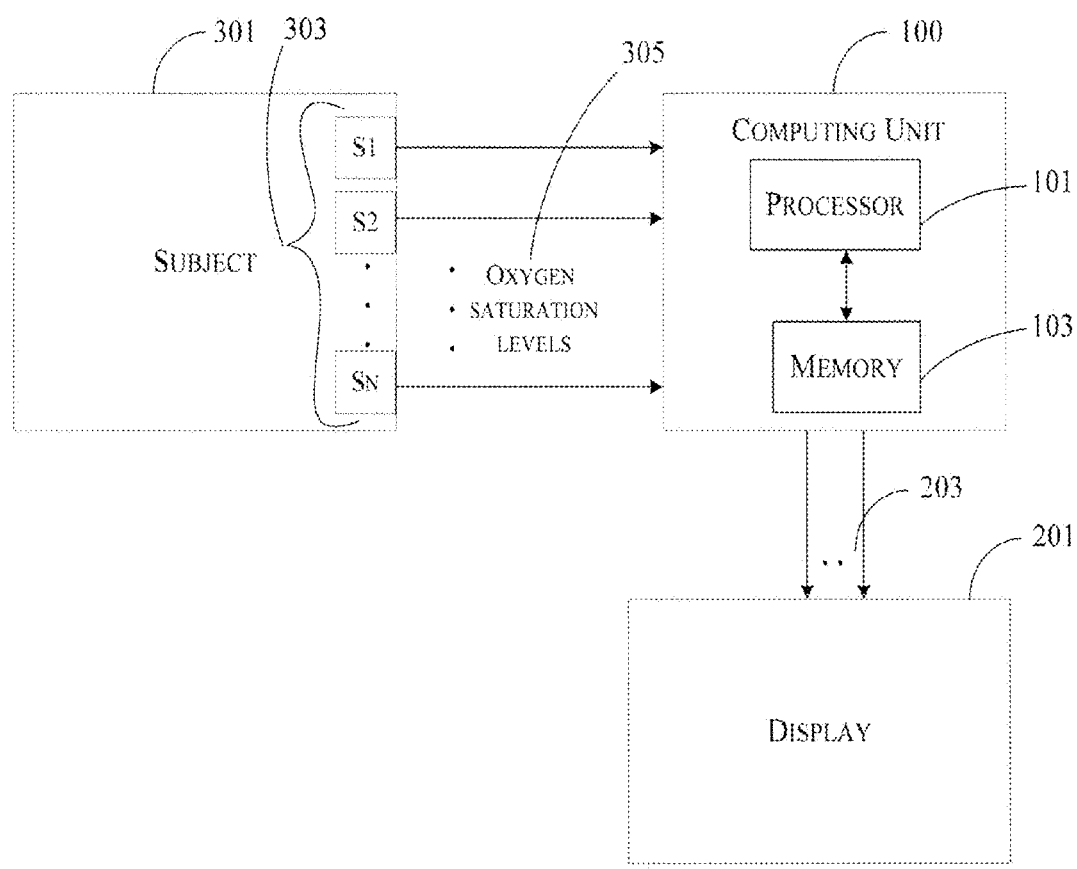
FIG. 3A illustrates an environment in which a computing unit receives physiological signals associated with a subject in accordance with some embodiments of the present disclosure.

FIG. 3A illustrates an environment in which a computing unit 100 receives signals associated with a subject in accordance with some embodiments of the present disclosure. The computing unit 100 may be configured to receive oxygen saturation levels 305 from a plurality of sensors (S1, S2 . . . Sn) 303 placed on the subject 301. The subject 301 may be one of a human being and an animal. The oxygen saturation levels may be received from plurality of sensors such as pulse oximetry sensors. A person skilled in the art would understand that any other sensor which provides oxygen saturation levels of blood can be used with the method of the present disclosure.

In an exemplary embodiment, the sensors 303 may be placed in the form of adhesive patches on the body of a subject 301 such as, but not limited to a worker or an employee. For example, a pulse oximetry sensor may be placed on the neck region of the worker. In particular, a first sensor is to be placed on the carotid artery and the second sensor is to be places on jugular vein.

The computing unit 100 may receive the signals 305 from the plurality of sensors (S1, S2 . . . Sn) 303, using either wired or wireless means. In one exemplary embodiment, the computing unit 100 may receive the physiological signals 305 using wireless radio technology such as, but not limited to, WiFi, Bluetooth and Zigbee. Further, the computing unit 100 may include a data aggregator for acquiring the physiological signals 305 from plurality of sensors 303. The data aggregator may be placed in the vicinity of the subject for data aggregation. Upon acquiring the physiological signals 305 by the data aggregator, the signals are stored in the memory 103 for further processing.

The processor 101 may estimate a mental fatigue level from the oxygen saturation levels 305 using sensor specific methodologies. The signals 305 are received by the computing unit 100 from the plurality of sensors 303, wherein each sensor signals are converted into digital data and queued by the data aggregator. The queued data is processed using sensor specific method. The estimated fatigue values are stored in the memory of the computing unit 101 for further processing.

The processor 101 computes the cerebral extraction of oxygen for each sample of oxygen saturation levels received for duration of predefined amount of time. Then, the processor 101 computes a median value of the sets of windowed data of cerebral extraction of oxygen. This is done to avoid outliers which are caused due to sampling or measurement errors.

Then processor 101 then analyzes the trend of cerebral extraction of oxygen to determine the health condition of the subject. The fatigue is a slow varying characteristic and, therefore, the values of CEO2 for a predefined amount of time are taken into consideration. For example, the CEO2 values of recent 5 minutes can be considered for analysis. In an embodiment, the CEO2 values are analyzed by comparing the CEO2 values with the threshold level.

In an embodiment, single threshold level may be used with the method of present disclosure. If the CEO2 value of the subject is substantially near or equal to the threshold level, then an alarm is generated by the computing unit 100 to notify the subject or any other system or person regarding the health condition of the subject.

The threshold levels may also be classified at least one of low threshold level, medium threshold level and high threshold level. As an example, the CEO2 of the subject can be compared with at least one of these levels to monitor health condition of the subject. In an embodiment, if the CEO2 value of the subject is substantially near or equal to the low threshold level, then the subject is considered to have low mental fatigue. In such a case, the subject can perform tasks without any difficulty/risk. If the CEO2 value of the subject is substantially near or equal to the medium threshold level, then the subject is considered to have medium mental fatigue. In such a case, the subject can perform tasks, however, fatigue level of the subject needs to be monitored continuously. In the alternative, if the CEO2 value is substantially near or equal to the high threshold level, then the subject needs to take rest and should not be allowed to perform tasks that require concentration.

The threshold level may be created based on a population database. The population database comprises values of cerebral extraction of oxygen for a large population with various age groups. These values are used to create the threshold levels for different age groups. The below table, Table 1 shows exemplary values of threshold levels for different age groups.

TABLE 1

| Age (in years) | Low threshold level | Medium threshold level | High threshold level |
|---|---|---|---|
| <20 | 80 | 85 | 90 |
| 20-30 | 75 | 80 | 85 |
| 30-40 | 70 | 80 | 85 |
| 40-50 | 65 | 75 | 80 |
| 50-70 | 60 | 70 | 75 |
| >70 | 50 | 60 | 70 |

In an embodiment, the threshold levels may be personalized for each subject, as different subjects have different health conditions and the fatigue level may not be same for all the subjects. The threshold levels may be personalized for a subject by considering CEO2 levels of the subject during resting, normal activity and restlessness scenarios over a period of time.

As an example of personalization of the threshold values, the PERSONAL_OFFSET of a subject can be calculated using the CEO2 value during rest. For different subjects of same age group, the range of CEO2 may vary depending on the variations in the blood flow to brain. This can be normalized by using the PERSONAL_OFFSET. The final CEO2 value for trend analysis is calculated as shown below:

$$\text{PERSONAL\_OFFSET} = \text{Individual\_Rest\_CEO2} - \text{Population\_Rest\_CEO2} \quad (2)$$

$$\text{Final\_CEO2\_Val} = \text{Measured\_CEO2} - (\text{Wt1} * \text{PERSONAL\_OFFSET}) \quad (3)$$

where,

Individual_Rest_CEO2 is CEO2 measured during resting of the individual,

Population_Rest_CEO2 is CEO2 of the population database of similar age group during rest, Measured_CEO2 is CEO2 of the individual measured using carotid artery and jugular vein blood saturation values, and Wt1 is weightage given to personal offset value which ranges from 0 to 1. In an embodiment, the weightage is assigned based on information in the population database.

Figure 4A:
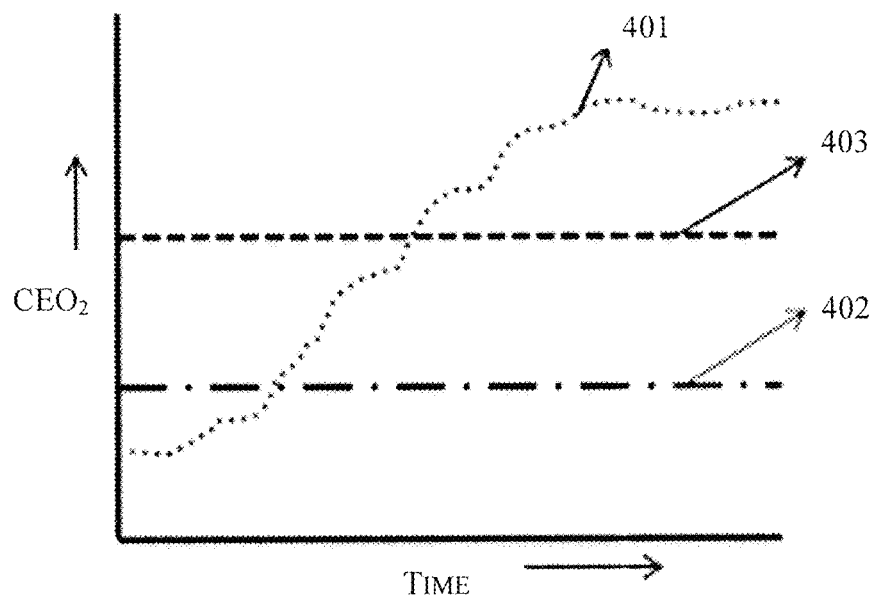
FIGS. 4A and 4B illustrate exemplary fatigue charts representing of a mental fatigue level of a subject in accordance with some embodiments of the present disclosure.
Figure 4B:
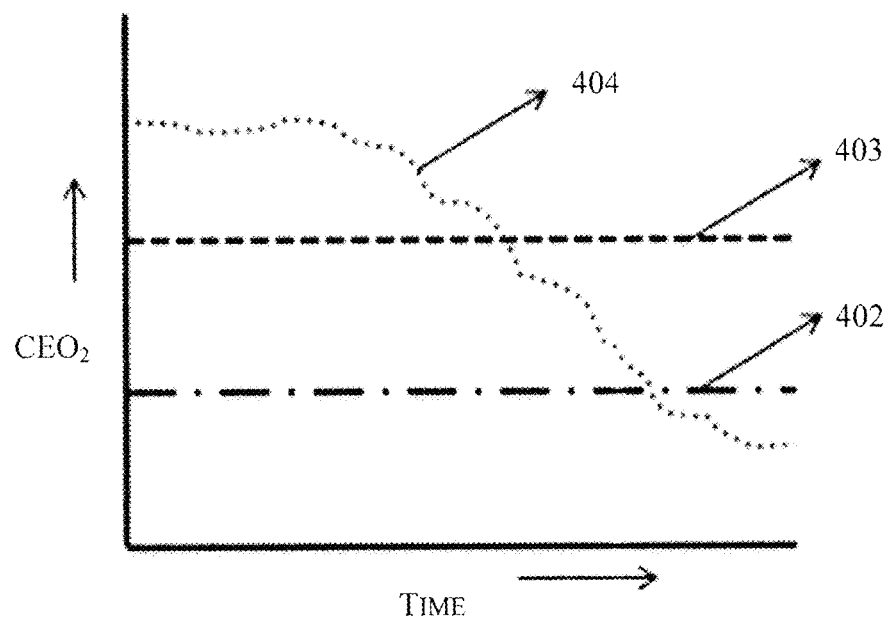

Upon comparison of the CEO2 values with the threshold levels, the processor 101 identifies a mental fatigue level of the subject. The mental fatigue level indicates the health condition of the subject. After determining the health condition of the subject, the processor 101 may display the mental fatigue level on the associated display unit 203. FIGS. 4A and 4B illustrate exemplary fatigue charts representing mental fatigue level of a subject in accordance with some embodiments of the present disclosure. FIG. 4A illustrates an increasing fatigue condition 401 for a subject, where the mental fatigue level of the subject is increasing with time. FIG. 4B illustrates decreasing fatigue condition 404 for a subject, where the mental fatigue level of the subject is decreasing with time. In both the fatigue charts, only two threshold levels, i.e. medium threshold level 402 and high threshold level 403 have been considered for determining health condition of the patient. Using the trend in the fatigue chart, the supervisor of the subject may change or reschedule the worker-job assignments for the subject.

In some embodiments of the present disclosure, the computing unit 100 may generate an alarm to indicate of the mental CEO2 level is above nearing, equal or above the predefined threshold level. The alarm may be displayed using image, video, text on the display 201. Also, the alarm may be provided to the subject or other system using an audio.

In an embodiment, the computing unit 100 detects a measurement error while determining the mental fatigue level. The status of the mental fatigue level at each time interval may be aggregated and analyzed to avoid any spurious or false values. Also, the analyzing of the status would help in generating realistic mental fatigue status. As an example, statistical models such as Bayes theorem may be used for detecting the measurement error while determining the mental fatigue level.

An exemplary scenario of aggregated mental fatigue status over a period of time is shown below. Here each value indicates the status of mental fatigue during a time window of 'X' minutes, say 5 minutes.

| N | N | N | M | M | M | H | H | H | H |
|---|---|---|---|---|---|---|---|---|---| where,

N—Normal

M—Medium Fatigue

S—High Fatigue

For example, the status continuously shows medium fatigue for 5 minutes and in between there is one high fatigue status. In such a case, the high fatigue status may be due to measurement error. This may happen if the sensor is defective, the sensor is not placed properly on the subject, transmission error etc. This information may be passed as input to the post processing to evaluate real fatigue situation.

Figure 3B:
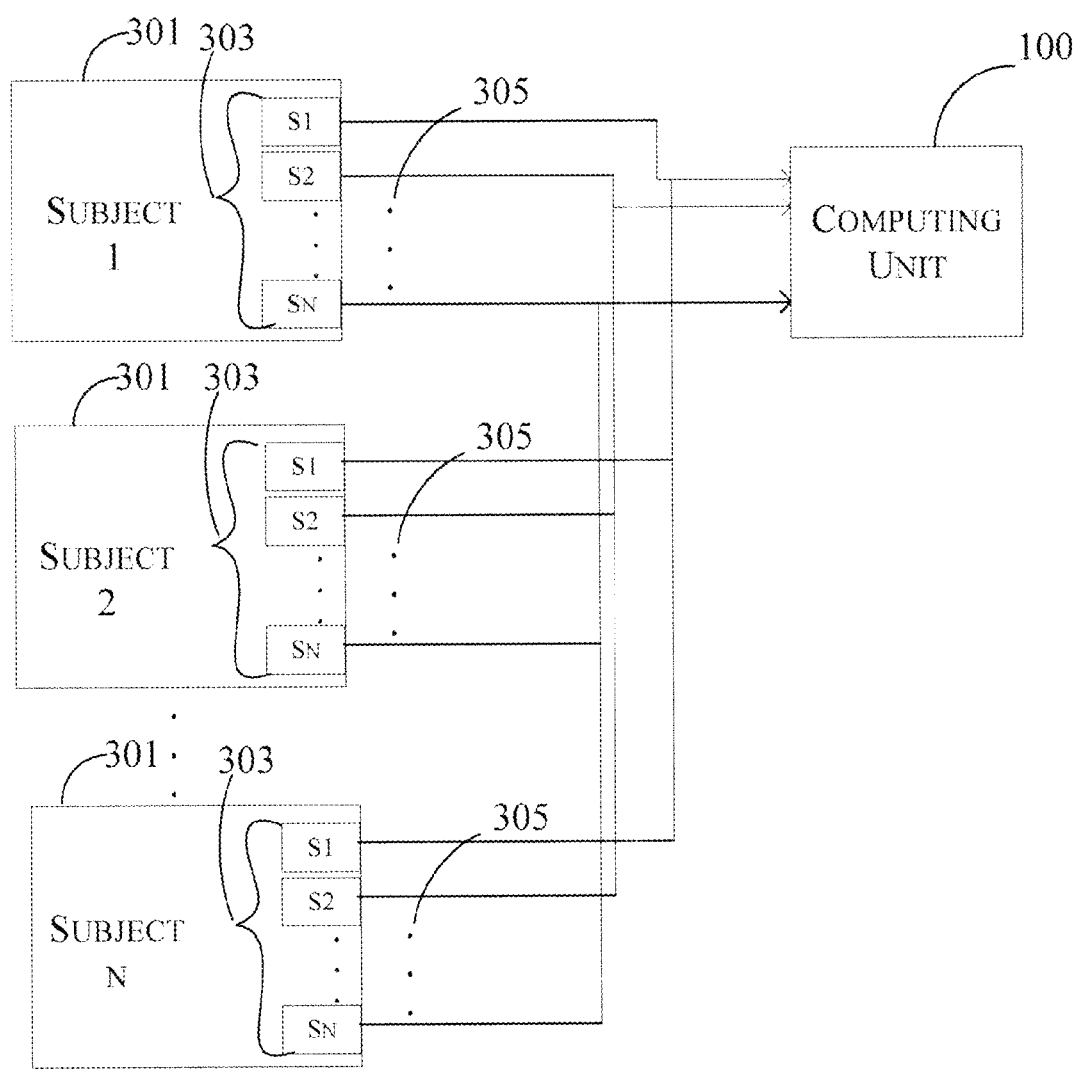
FIG. 3B illustrates an environment in which a computing unit receives physiological signals from a plurality of subjects in accordance with some embodiments of the present disclosure.

FIG. 3B illustrates an environment in which a computing unit 100 receives oxygen saturation levels 305 from a plurality of subjects (subject 1, subject 2 . . . subject n) 301 in accordance with some embodiments of the present disclosure. The computing unit 100 includes at least one processor 101 and a memory 103 storing instructions executable by the at least one processor 101. Initially, the processor 101 determines cerebral extraction of oxygen using the oxygen saturation levels. Thereafter, the processor 101 identifies the mental fatigue level of the subject by comparing the cerebral extraction of oxygen with a threshold level. The mental fatigue level indicates the health condition of the subject.

The computing unit may further comprise an alert system for generating an alarm. In some embodiment, the fatigue information of each subject or worker may be displayed on a display 201 by the computing unit 100.

Figure 5:
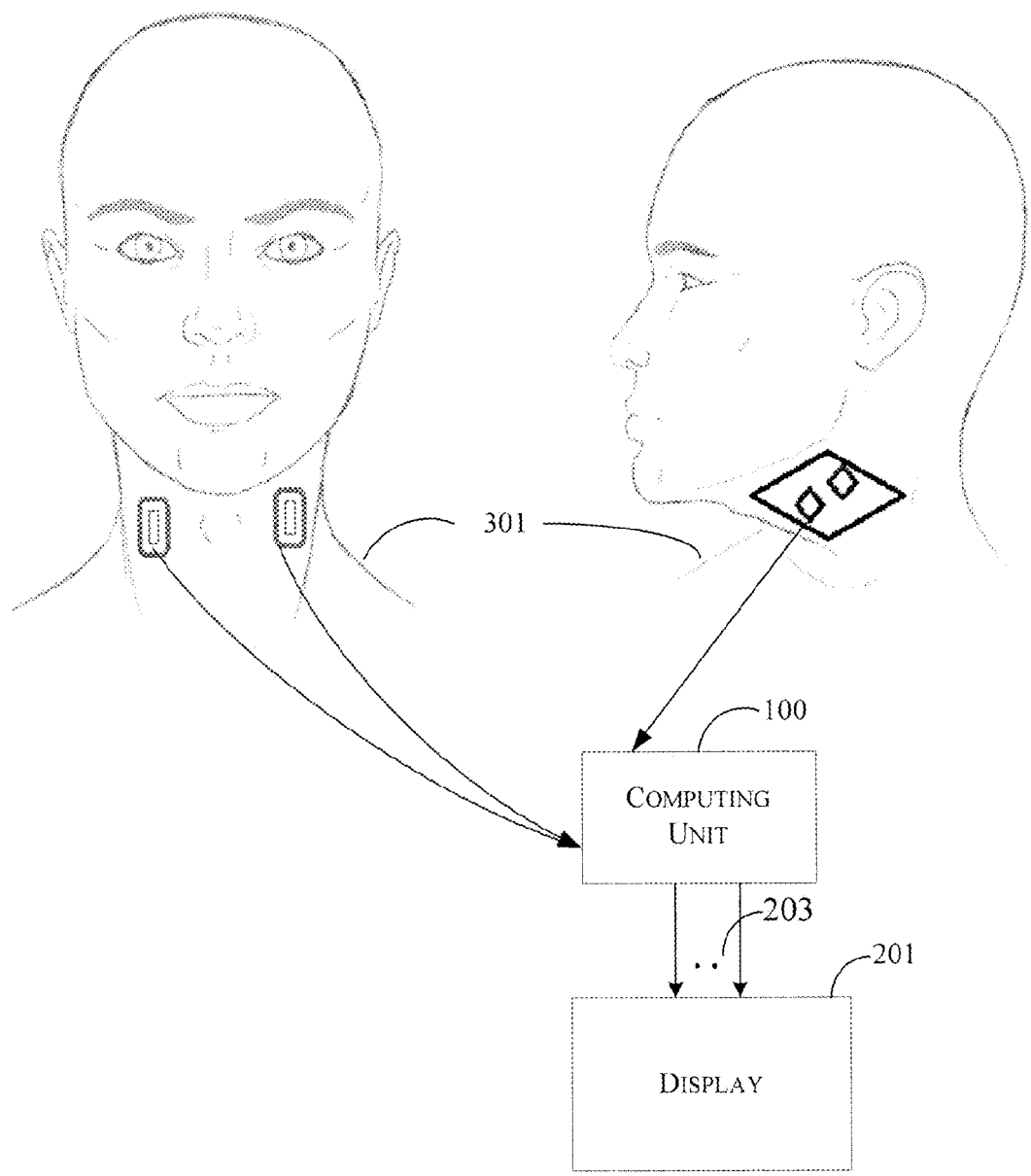
FIG. 5 illustrates an exemplary environment in which health condition of a human is monitored using an exemplary computing unit in accordance with an example embodiment of the present disclosure.

FIG. 5 illustrates an exemplary computing unit 100 to monitor health condition of a human 301 along with an associated display 201 in accordance with an example embodiment of the present disclosure. The computing unit 100 may be configured to receive oxygen saturation levels 305 from a plurality of sensors (S1, S2 . . . Sn) 303 placed on the human 301. Particularly, in the illustrated figure, two sensors are placed on the neck of the subject using a patch. The sensors may be placed on sides of the neck. Also, the two sensors may be put on a single patch and placed on one side of the neck. In some exemplary embodiments, the oxygen saturation levels may be transmitted by a transmitter 501 placed along with the plurality of sensors, on the body of human 301.

Figure 6:
FIG. 6 shows a flowchart illustrating a method of determining health condition of a subject using a computing device in accordance with some embodiments of the present disclosure.

FIG. 6 shows a flowchart illustrating a method for determining health condition of a subject using a computing unit in accordance with some embodiments of the present disclosure.

As illustrated in FIG. 6, the method 600 comprises one or more blocks for determining health condition of a subject by the computing unit 100. The method 600 may be described in the general context of computer executable instructions. Generally, computer executable instructions can include routines, programs, objects, components, data structures, procedures, modules, and functions, which perform particular functions or implement particular abstract data types.

The order in which the method 600 is described is not intended to be construed as a limitation, and any number of the described method blocks can be combined in any order to implement the method 600. Additionally, individual blocks may be deleted from the method 600 without departing from the spirit and scope of the subject matter described herein. Furthermore, the method 600 can be implemented in any suitable hardware, software, firmware, or combination thereof.

At block 610, receive a first oxygen saturation level and a second oxygen saturation level from at least two sensors placed on the subject. The at least two sensors of sensors are placed on neck of the subject. The subject may be one of human and animal. In an embodiment, the first oxygen saturation level is oxygen saturation level in the incoming blood flow via carotid artery of the subject. The second oxygen saturation level is oxygen saturation level in an outgoing blood flow via jugular vein of the subject. The first oxygen saturation level and the second oxygen saturation level are received at a predefined time interval from the at least two sensors.

At block 620, determine cerebral extraction of oxygen using the first and second oxygen saturation levels. The cerebral extraction of oxygen is determined by a difference between the first and the second oxygen saturation levels At block 630, compare the cerebral extraction of oxygen with a threshold level. The threshold level may be classified as at least one of low threshold level, medium threshold level and high threshold level.

At block 640, identify a mental fatigue level of the subject based on outcome of the comparison. The comparison of the cerebral extraction of oxygen with the threshold levels provides a mental fatigue level of the subject. The mental fatigue level indicates the health condition of the subject. In an embodiment, if the mental fatigue level is greater than at least one of medium threshold level and high threshold level, the computing unit generates an alarm signal. The alarm signal may be provided to display unit in form of audio/image/video.

Computer System

Figure 7:
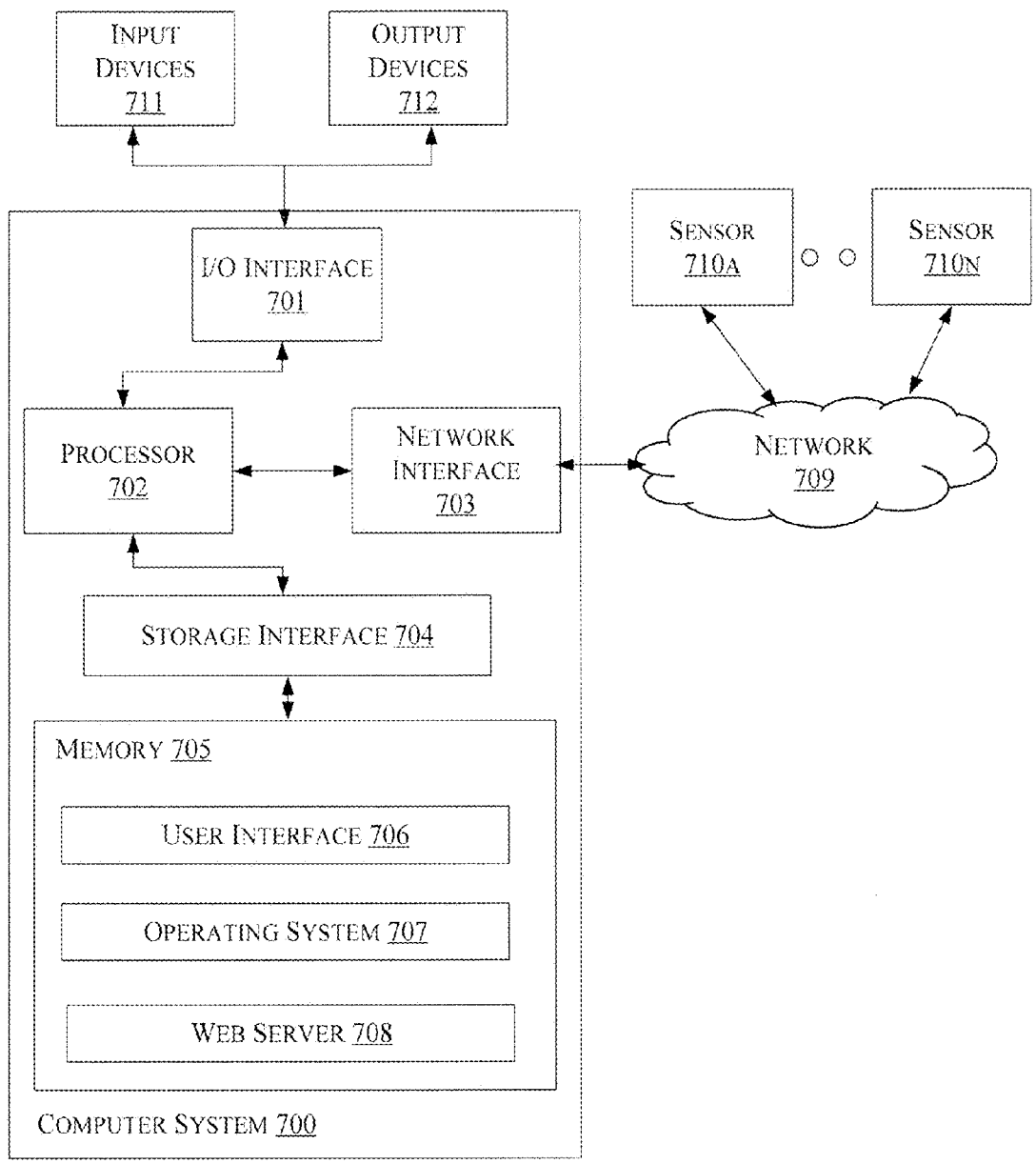
FIG. 7 illustrates a block diagram of an exemplary computer system for implementing embodiments consistent with the present disclosure.

FIG. 7 illustrates a block diagram of an exemplary computer system 700 for implementing embodiments consistent with the present disclosure. In an embodiment, the computer system 700 is used to implement the computing unit 100. The computer system 700 monitors the health condition of a subject. The computer system 700 may comprise a central processing unit ("CPU" or "processor") 702. The processor 702 may comprise at least one data processor for executing program components for executing user- or system-generated business processes. A user may include a person, a person using a device such as those included in this disclosure, or such a device itself. The processor 702 may include specialized processing units such as integrated system (bus) controllers, memory management control units, floating point units, graphics processing units, digital signal processing units, etc.

The processor 702 may be disposed in communication with one or more input/output (I/O) devices (711 and 712) via I/O interface 701. The I/O interface 701 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 701, the computer system 700 may communicate with one or more I/O devices (711 and 712). For example, the input device 711 may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device 712 may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the processor 702 may be disposed in communication with a communication network 709 via a network interface 703. The network interface 703 may communicate with the communication network 709. The network interface 703 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 709 may include, without limitation, a direct interconnection, local area network (LAN), wide area network (WAN), wireless network (e.g., using Wireless Application Protocol), the Internet, etc. Using the network interface 703 and the communication network 709, the computer system 700 may communicate with data aggregator or sensors 710.

In some embodiments, the processor 702 may be disposed in communication with a memory 705 (e.g., RAM, ROM, etc. not shown in FIG. 7) via a storage interface 704. The storage interface 704 may connect to memory 705 including, without limitation, memory drives, removable disc drives, etc., employing connection protocols such as serial advanced technology attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 705 may store a collection of program or database components, including, without limitation, user interface application 706, an operating system 707, web server 708 etc. In some embodiments, computer system 700 may store user/application data 706, such as the data, variables, records, etc. as described in this disclosure. Such databases may be implemented as fault-tolerant, relational, scalable, secure databases such as Oracle or Sybase.

The operating system 707 may facilitate resource management and operation of the computer system 700. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 717 may facilitate display, execution, interaction, manipulation, or operation of program components through textual or graphical facilities. For example, user interfaces may provide computer interaction interface elements on a display system operatively connected to the computer system 700, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 700 may implement a web browser 708 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 700 may implement a mail server 719 stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 700 may implement a mail client stored program component. The mail client may be a mail viewing application, such as Apple Mail, Microsoft Entourage, Microsoft Outlook, Mozilla Thunderbird, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible, non-transitory items and exclude carrier waves and transient signals. Examples include Random Access Memory (RAM), Read-Only Memory (ROM), volatile memory, nonvolatile memory, hard drives, CD ROMs, DVDs, flash drives, disks, and any other known physical storage media.

Advantages of the embodiment of the present disclosure are illustrated herein.

Embodiment of the present disclosure provides noninvasive measurement of mental fatigue of a subject.

The method of present disclosure measuring oxygen saturation levels of carotid artery and jugular vein provides more reliable readings of mental fatigue as fatigue is state of brain's alertness.

In an embodiment of the present disclosure, any measurement errors while determining the mental fatigue level can be detected.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media comprise all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices. An "article of manufacture" comprises non-transitory computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the invention, and that the article of manufacture may comprise suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 6 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method for determining a health condition, the method comprising:
   receiving, by a health monitoring computing device, a first oxygen saturation level and a second oxygen saturation level from at least two sensors disposed proximate a subject;
   determining, by the health monitoring computing device, a level of cerebral extraction of oxygen using the first and second oxygen saturation levels;
   comparing, by the health monitoring computing device, the level of cerebral extraction of oxygen with thresholds, wherein the thresholds are personalized for the subject based on the level of cerebral extraction of oxygen of the subject during each of a resting state, a normal state and a restlessness state of the subject over a period of time; and
   identifying and outputting, by the health monitoring computing device, a mental fatigue level of the subject based on the comparison, wherein the mental fatigue level indicates the health condition of the subject.

2. The method as claimed in claim 1, wherein the first oxygen saturation level and the second oxygen saturation level are received at a predefined time interval.

3. The method as claimed in claim 1, wherein the level of cerebral extraction of oxygen is determined based on a difference between the first and the second oxygen saturation levels.

4. The method as claimed in claim 1, wherein the first oxygen saturation level is an oxygen saturation level in the incoming blood flow via a carotid artery of the subject and the second oxygen saturation level is an oxygen saturation level in an outgoing blood flow via a jugular vein of the subject.

5. The method as claimed in claim 1, wherein the thresholds comprise a low threshold, a medium threshold level, and a high threshold and the method further comprises generating, by the health monitoring computing device, an alarm if the mental fatigue level is greater than at least one of the medium threshold or the high threshold.

6. The method as claimed in claim 1, wherein the thresholds are personalized based on at least one of an age of the subject or historical data of a cerebral extraction of oxygen of the subject.

7. A health monitoring computing device, comprising:
   a processor; and
   a memory communicatively coupled to the processor, wherein the memory stores processor instructions, which, on execution, causes the processor to:
      receive a first oxygen saturation level and a second oxygen saturation level from at least two sensors disposed proximate a subject;
      determine a level of cerebral extraction of oxygen using the first and second oxygen saturation levels;
      compare the level of cerebral extraction of oxygen with thresholds, wherein the thresholds are personalized for the subject based on the level of cerebral extraction of oxygen of the subject during each of a resting state, a normal state and a restlessness state of the subject over a period of time; and identify and output a mental fatigue level of the subject based on the comparison, wherein the mental fatigue level indicates the health condition of the subject.

8. The health monitoring computing device as claimed in claim 7, wherein the first oxygen saturation level and the second oxygen saturation level are received at a predefined time interval.

9. The health monitoring computing device as claimed in claim 7, wherein the level of cerebral extraction of oxygen is determined based on a difference between the first and the second oxygen saturation levels.

10. The health monitoring computing device as claimed in claim 7, wherein the first oxygen saturation level is an oxygen saturation level in the incoming blood flow via a carotid artery of the subject and the second oxygen saturation level is an oxygen saturation level in an outgoing blood flow via a jugular vein of the subject.

11. The health monitoring computing device as claimed in claim 7, wherein the thresholds comprise a low threshold, a medium threshold level, and a high threshold and the processor coupled to the memory is further configured to be capable of executing at least one additional programmed instruction comprising and stored in the memory to generate an alarm if the mental fatigue level is greater than at least one of the medium threshold or the high threshold.

12. The health monitoring computing device as claimed in claim 7, wherein the thresholds are personalized based on at least one of an age of the subject or historical data of a cerebral extraction of oxygen of the subject.

13. A non-transitory computer readable medium having stored thereon instructions for determining a health condition comprising executable code which when executed by a processor, causes the processor to perform steps comprising:

receiving a first oxygen saturation level and a second oxygen saturation level from at least two sensors disposed proximate a subject;

determining a level of cerebral extraction of oxygen using the first and second oxygen saturation levels;

comparing the level of cerebral extraction of oxygen with thresholds, wherein the thresholds are personalized for the subject based on the level of cerebral extraction of oxygen of the subject during each of a resting state, a normal state and a restlessness state of the subject over a period of time; and identifying and outputting a mental fatigue level of the subject based on the comparison, wherein the mental fatigue level indicates the health condition of the subject.

14. The non-transitory computer readable medium as claimed in claim 13, wherein the first oxygen saturation level and the second oxygen saturation level are received at a predefined time interval.

15. The non-transitory computer readable medium as claimed in claim 13, wherein the level of cerebral extraction of oxygen is determined based on a difference between the first and the second oxygen saturation levels.

16. The non-transitory computer readable medium as claimed in claim 13, wherein the first oxygen saturation level is an oxygen saturation level in the incoming blood flow via a carotid artery of the subject and the second oxygen saturation level is an oxygen saturation level in an outgoing blood flow via a jugular vein of the subject.

17. The non-transitory computer readable medium as claimed in claim 13, wherein the thresholds comprise a low threshold, a medium threshold level, and a high threshold and the executable code when executed by the processor further causes the processor to perform at least one additional step comprising generating an alarm if the mental fatigue level is greater than at least one of the medium threshold or the high threshold.

18. The non-transitory computer readable medium as claimed in claim 13, wherein the thresholds are personalized based on at least one of an age of the subject or historical data of a cerebral extraction of oxygen of the subject.

* * * * *